United States Patent [19]

Teissen-Simony

[11] Patent Number: 5,522,803

[45] Date of Patent: Jun. 4, 1996

[54] INFUSION SET FOR AN INTERMITTENT OR CONTINUOUS ADMINISTRATION OF A THERAPEUTICAL SUBSTANCE

[75] Inventor: Claude Teissen-Simony, Copenhagen, Denmark

[73] Assignee: Pharma Plast International A/S, Denmark

[21] Appl. No.: 522,318

[22] PCT Filed: Mar. 8, 1994

[86] PCT No.: PCT/DK94/00098

§ 371 Date: Sep. 5, 1995

§ 102(e) Date: Sep. 5, 1995

[87] PCT Pub. No.: WO94/20160

PCT Pub. Date: Sep. 15, 1994

[30] Foreign Application Priority Data

Mar. 9, 1993 [DK] Denmark ................. 0257/93

[51] Int. Cl.⁶ .................................. A61M 5/32
[52] U.S. Cl. ................. 604/177; 604/174; 604/93; 604/890.1
[58] Field of Search ................. 604/174–175, 604/177, 93, 239–240, 241–243

[56] References Cited

U.S. PATENT DOCUMENTS

| | | |
|---|---|---|
| 4,352,354 | 10/1982 | Ujihara . |
| 4,362,156 | 12/1982 | Feller, Jr. et al. . |
| 4,863,432 | 9/1989 | Kvalo . |
| 5,186,712 | 2/1993 | Kelso et al. . |
| 5,267,967 | 12/1993 | Schneider . |

FOREIGN PATENT DOCUMENTS

0268480A1  5/1988  European Pat. Off. .

*Primary Examiner*—John D. Yasko
*Assistant Examiner*—Perry E. Van Over
*Attorney, Agent, or Firm*—Willian Brinks Hofer Gilson & Lione

[57] ABSTRACT

An infusion set for an intermittent or continuous administration of a therapeutical substance, such as insulin, comprises a cannula housing (1) with a soft plastic cannula (2) to be placed inside the body of a patient, where the cannula together with the cannula housing (1) form a through passageway the inlet of which into the cannula housing (1) is covered by a membrane. The infusion set comprises furthermore a needle hub (3) with a needle to be inserted in the through passageway of the cannula housing through the membrane. The infusion set comprises guide means for centering the needle relative to the membrane and the through passageway, as well as locking means (31, 32) for releasably interlocking the cannula housing (1) and the needle hub (3). In the assembled state the cannula housing (1) and the needle hub (3, 41) present a substantially planar rear side (6) and a relatively large width in a direction-parallel thereto and substantially perpendicular to the longitudinal central axis of the through passageway. The guide means are co-operating guide pins and guide openings on each side of the needle and the through passageway, and the locking means are resilient locking pins (31, 32) arranged on their respective side of the needle on the needle hub (3) and comprising barbs (33, 34), said locking pins with barbs being adapted to be received in their respective recess in the cannula housing (1), where said recesses comprise shoulders (25, 26) mating said barbs (33, 34).

8 Claims, 5 Drawing Sheets

INFUSION SET FOR AN INTERMITTENT OR CONTINUOUS ADMINISTRATION OF A THERAPEUTICAL SUBSTANCE

TECHNICAL FIELD

The invention relates to an infusion set for an intermittent or continuous administration of a therapeutical substance, such as insulin, said infusion set comprising a cannula housing with a soft plastic cannula to be placed inside the body of a patient, where the cannula together with the cannula housing form a through passageway the inlet of which into the cannula housing is covered by a membrane, and where said infusion set comprises a needle hub with a needle to be inserted in the through passageway of the cannula housing through the membrane, and furthermore guide means for centering the needle relative to the membrane and the through passageway, as well as locking means for releasably interlocking the cannula housing and the needle hub.

BACKGROUND ART

EP-PS No. 256,694 discloses an infusion set of the above type. This infusion set comprises a cannula housing, in which the membrane is placed relatively far down in the through passageway in the cannula housing, a passageway between the membrane and the end facing away from the cannula forming a guide for the needles to be inserted through said membrane. The entire infusion set is shaped in a substantially rotationally symmetrical manner about the longitudinal central axis of the through passageway.

WO 88/03816 discloses an infusion set with a membrane secured at the inlet to the through passageway through the cannula housing. The membrane is retained between a beaded or melted down portion of the material of the cannula housing and a bushing arranged immediately inside the membrane and forming a conical inlet to the continued portion of the through passageway to the cannula. This infusion set is also shaped in a substantially rotationally symmetrical manner about the longitudinal central axis of the through passageway.

BRIEF DESCRIPTION OF THE INVENTION

The object of the invention is to provide an infusion set being relatively easy to handle and easy to secure to the skin of the patient in question.

The infusion set of the above type is according to the invention characterised in that in the assembled state the cannula housing and the needle hub present a substantially planar rear side and a relatively large width in a direction parallel thereto and substantially perpendicular to the longitudinal central axis of the through passageway, that the guide means are co-operating guide pins and guide openings on each side of the needle and the through passageway, and that the locking means are resilient locking pins arranged on their respective side of the needle on the needle hub and comprising barbs, said locking pins with barbs being adapted to be received in their respective recess in the cannula housing, where said recesses comprise shoulders mating said barbs.

This infusion set is relatively easy to secure in a reliable manner to the skin of the patient, said set being arranged with the planar side abutting said skin. In addition, it is relatively easy to handle because the guide means ensure an easy alignment and centering of the needle of the needle hub relative to the membrane of the cannula housing before said membrane is penetrated. Finally, the resilient locking pins ensure a relatively easy snap-engagement and interlocking of the cannula housing and the needle hub, and this engagement is easily releasable again due to the resilience of the locking pins. An easy access to the membrane of the reliably retained cannula housing is possible by a removal of the needle hub so as to allow an insertion of the needle on a syringe, if any, to be used shortly for administration of a therapeutical substance. A coupling through a hose of the needle hub to a pump, such as an insulin pump, renders it possible to easily connect said pump with the cannula housing through the needle hub.

According to the invention, the cannula housing and the needle hub may in the assembled state be of a substantially circular shape with a substantially uniform thickness, the cannula housing being formed integral with a projecting platform substantially covering the entire rear side of the needle hub in the assembled state. In this manner a particularly simple embodiment of the infusion set is obtained, and the cannula housing is relatively easy to secure to the body of the patient by means of plaster or the like tape provided with glue. Inter alia the projecting platform provides a suitable surface for such a plaster because said plaster is placed across said platform and is well protected below the needle hub when said needle hub is correctly positioned and engages the cannula housing. A second plaster may be placed across the cannula housing presenting a good surface for said plaster due to its relatively flat shape. Alternatively, an adhesive layer can be placed on the rear side of the cannula housing with the projecting platform.

Furthermore according to the invention, the cannula housing and the needle hub may in the assembled state be divided along a substantially diametrically extending plane, which extends perpendicular to the central axis of the needle and the through passageway, whereby the inlet to the through passageway and to the guide openings provided in the cannula housing is shaped in a projection extending perpendicular from the diametrical plane and into a corresponding recess in the needle hub. In this manner a well-suited embodiment is obtained, which is easy to handle in particular in view of the dimensions usually being relatively small, i.e. the external diameter being approximately 21 mm and the height being approximately 5 mm. The presence of the projection with the inlet to the through passageway and to the guide openings in the cannula housing as well as the corresponding recess in the needle hub allow a relatively large length of said members, such as needle, guide openings and guide pins co-operating therewith with the effect that the necessary guiding of the needle in question is ensured. Furthermore it is ensured that the needle completely penetrates the membrane when used.

Moreover according to the invention, the guide pins and the associated guide openings and the locking pins and the associated recesses may be symmetrically shaped relative to a central plane perpendicular to the plane rear side and coinciding with the longitudinal central axis of the needle and the through passageway, respectively. As a result, a particularly simple embodiment of the invention is obtained.

Furthermore according to the invention the locking pins and the guide pins may be placed on the needle hub, and the barbs of the locking pins may face away from one another, as well as symmetrically shaped recesses may be provided between the locking pins and the guide pins so as to increase the resilience of said locking pins. In this manner a particularly easy release of the engagement of the locking pins with the associated shoulders on the cannula housing is obtained.

According to the invention the recesses receiving the locking pins may everywhere be of a larger sectional area than the locking pins and at the bottom immediately adjacent the shoulders co-operating with the barbs on said locking pins the recesses may be connected with the top side of the portion of the infusion set in question through an opening. In this manner a particularly easy rinsing of dust particles is ensured during bathing, as well as the risk of said dust particles depositing has been minimized.

According to the invention it is particularly preferred that the longitudinal central axis of the through passageway inclines relative to the plane rear side, the inlet end with the membrane being positioned farthest away from said plane rear side relative to the location where the cannula exits the cannula housing, and the guide means, the locking means, and the needle on the needle hub may incline correspondingly at the same time. As a result, a relatively easy insertion of a needle in the flat cannula housing abutting the skin of the patient is ensured.

According to the invention the needle hub with the needle may be shaped in form of an inserter needle hub to be used when the cannula of the cannula housing is to be placed in the body of the patient, the needle of the inserter needle hub extending all through the through passageway and projecting outside the free end of the cannula, and at the same time the inserter needle hub may comprise an extension projecting away from the locking means and facilitating the handling of the infusion set during the placing. In this manner it is easy to place the cannula housing with the soft cannula on the patient by means of an inserter needle hub having a good an reliable grip in said cannula housing. After the placing, the inserter needle hub is relatively easily removed.

BRIEF DESCRIPTION OF THE DRAWING

The invention is explained in greater detail below with reference to the accompanying drawing, in which.

BEST MODE FOR CARRYING OUT THE INVENTION

Figure 1:
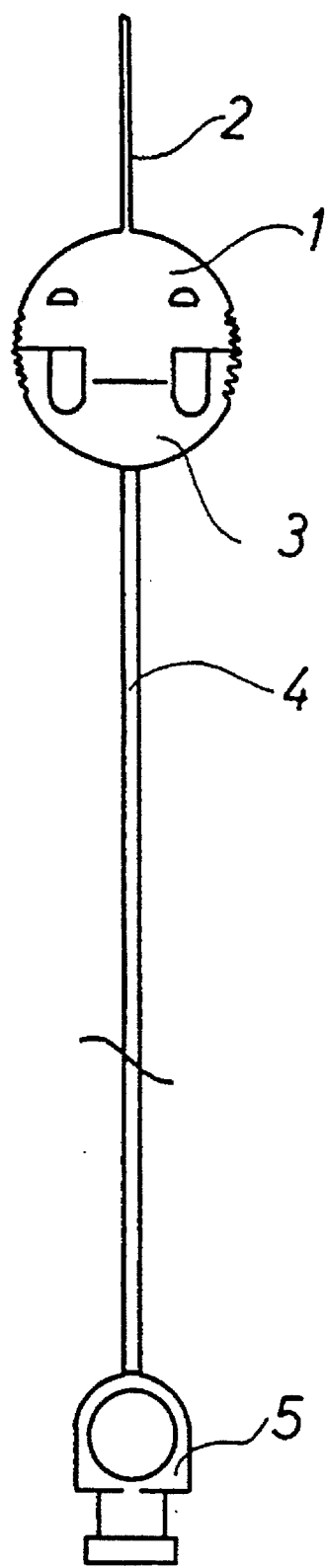
FIG. 1 is a front view of an infusion set according to the invention, connected to a hose with a luer coupling to be connected with a pump.
Figure 2:
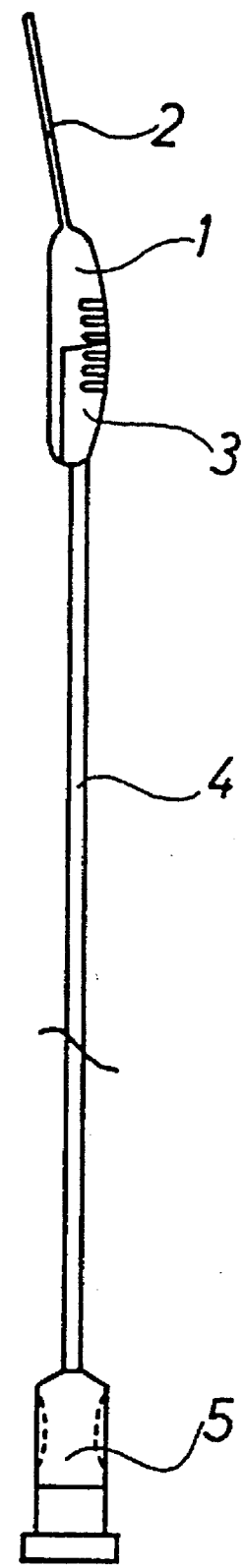
FIG. 2 is a side view of the infusion set of FIG. 1.

The infusion set of FIGS. 1 and 2 comprises a cannula housing 1 with a soft cannula 2 secured therein and manufactured in a conventional manner of a suitable plastic material. The infusion set comprises furthermore a connecting hub 3 connected in a conventional manner through a hose 4 with a luer coupling member 5 to be used at the coupling thereof to an insulin pump not shown.

Figure 3:
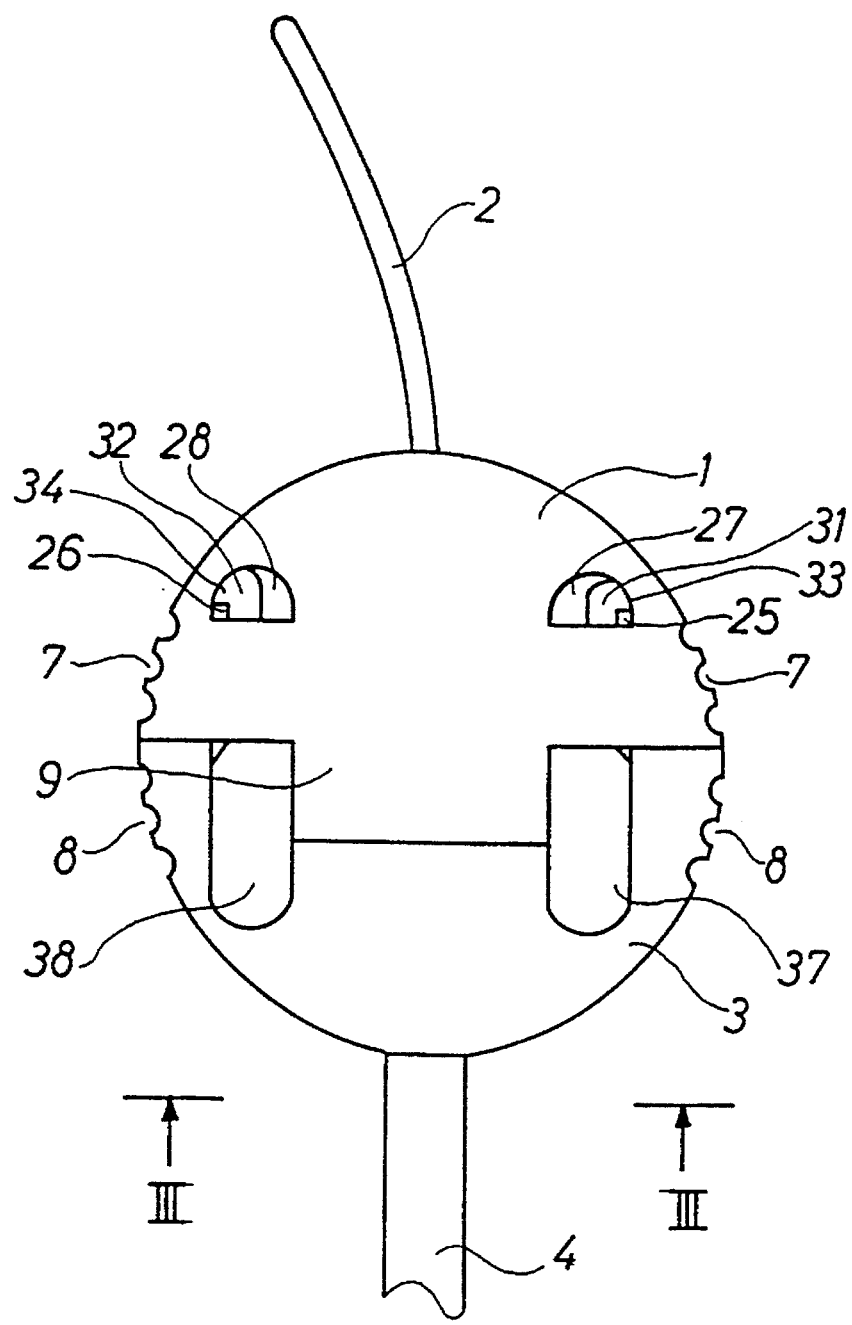
FIG. 3 illustrates on a larger scale the infusion set of FIG. 1.
Figure 4:
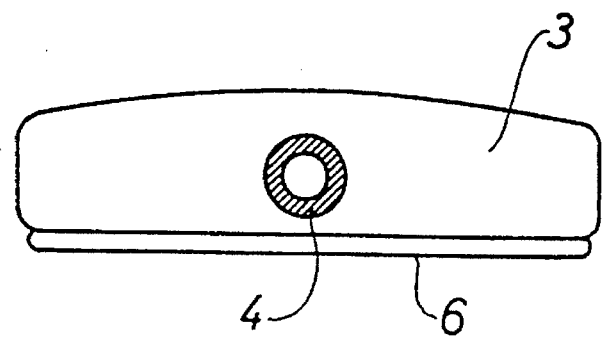
FIG. 4 is a bottom view taken along the, line III—III of the infusion set of FIG. 3.

FIGS. 3 and 4 show the cannula housing 1 and the connecting hub 3 on a larger scale. It appears clearly that together they are of a relatively flat shape and of a uniform thickness and a substantially plane rear side 6. When seen from the top, they are together of a substantially circular shape, said shape only being interrupted by some recesses 7 and 8, respectively, for facilitating a finger-handling. As illustrated in FIG. 3, the cannula housing 1 and the connecting hub 3 are substantially divided along a diametrical central plane, a central projection 9 being provided on said cannula housing 1 and projecting into a mating recess in the connecting hub 3. In FIG. 3, the cannula 2 is slightly curved in order to illustrate that it is bendable.

The cannula housing 1 and the connecting hub 3 are described in greater detail below with reference to the following Figures.

Figure 5:
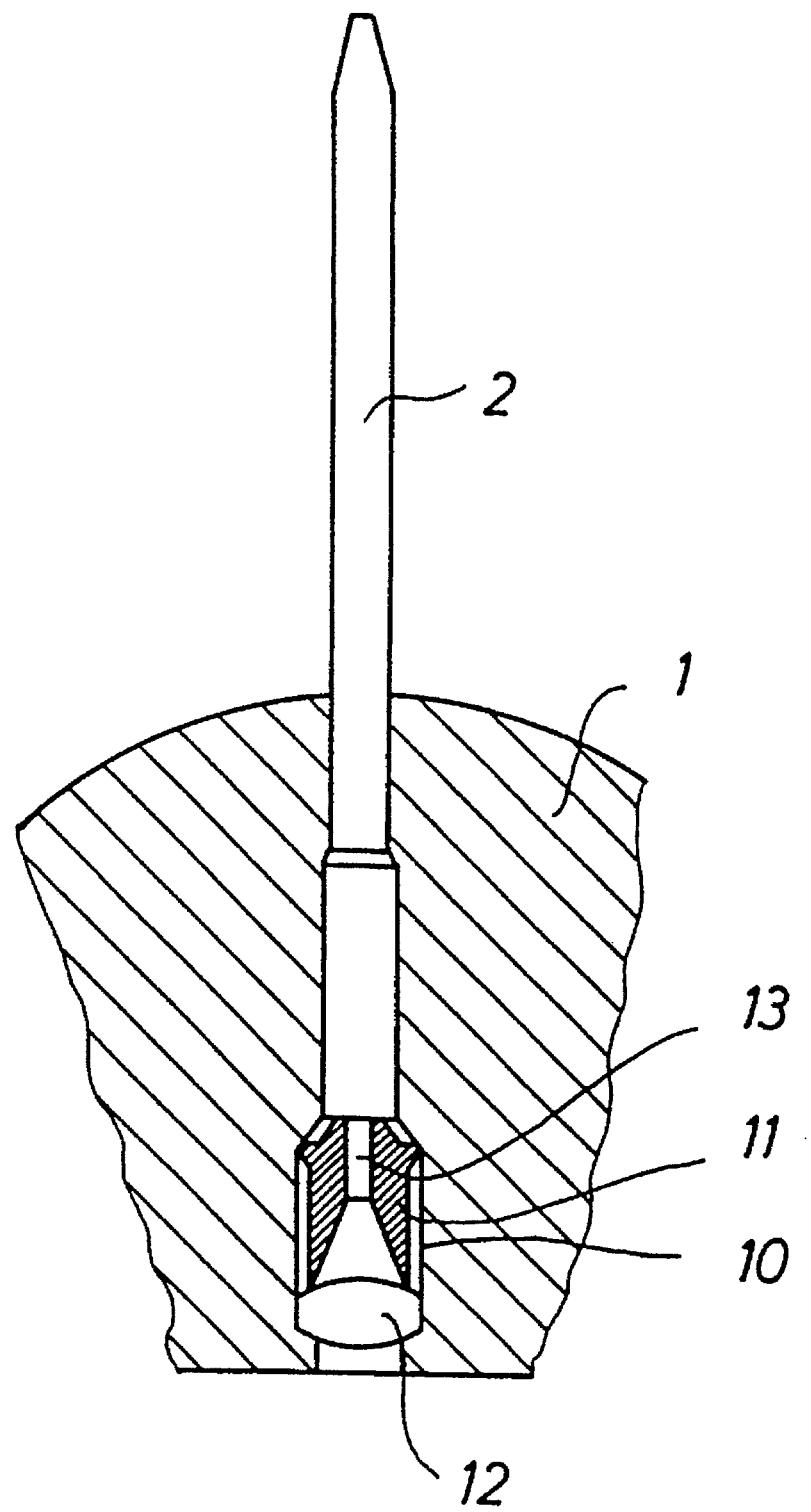
FIG. 5 is a sectional view on a larger scale through the cannula housing of the infusion set in a portion about a through passageway in which the cannula of the cannula housing is mounted.
Figure 6:
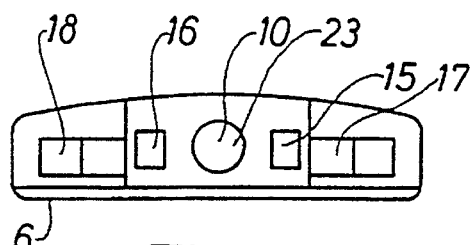
FIG. 6 illustrates the cannula housing seen from the end opposite the cannula.
Figure 7:
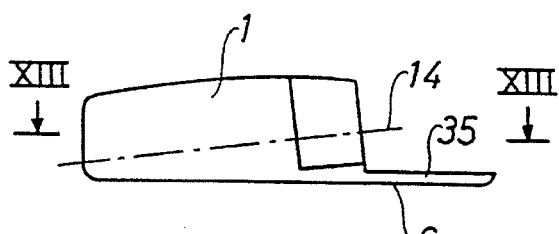
FIG. 7 is a side view of the cannula housing of FIG. 6, where the cannula has been removed.

As illustrated in FIG. 5, the cannula 2 is arranged in a rectilinear bore 10 through the cannula housing 1. This bore 10 decreases stepwise when seen from below and upwards relative to FIG. 5. The cannula 2 is clamped in an extension in the through bore by means of an axially projecting portion of a bushing 11. At the end opposite the cannula 2, the bushing 11 abuts a membrane 12 retained against the bushing 11 by means of a beaded or melt down portion of the cannula housing which is made of a suitable plastic material, such as polypropylene. The cannula 2, the bushing 11, and the membrane 12 in the cannula housing 1 are mounted in a conventional manner as described in the above WO 88/03816. The bushing 10 and the cannula 2 define a through passageway 13 with a longitudinal central axis designated the reference numeral 14 in the following Figures, FIGS. 6 to 10 illustrating the cannula housing 1 without a cannula 2 and membrane 11.

Figure 8:
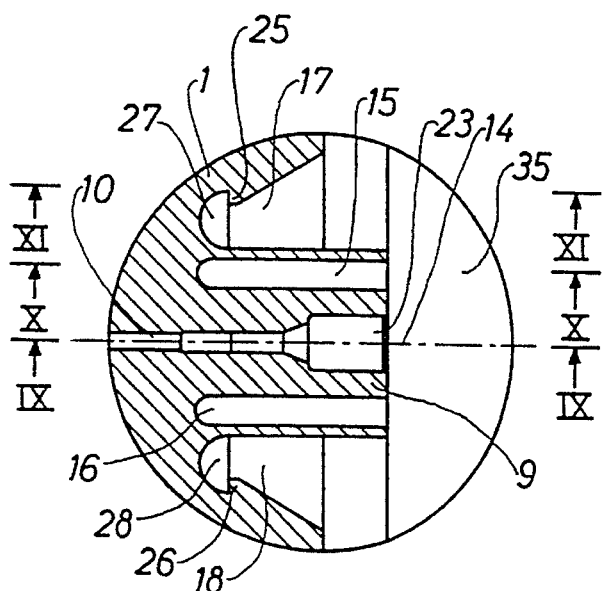
FIG. 8 is a sectional view taken along the line VIII—VIII of FIG. 7.
Figure 9:
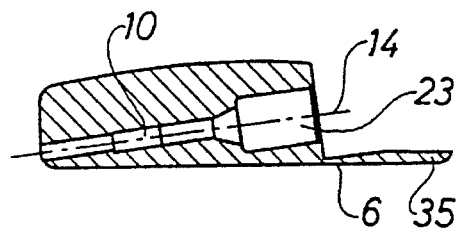
FIG. 9 is a sectional view taken along the line IX—IX if FIG. 8 and showing the through passageway for receiving the cannula not shown as well as a membrane not shown either.
Figure 10:
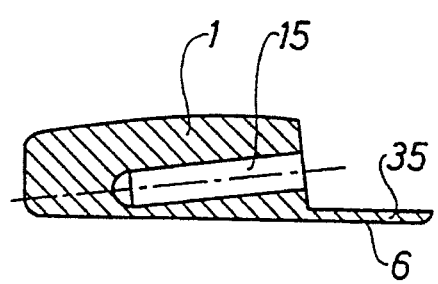
FIG. 10 is a sectional view taken along the line X—X of FIG. 8.

As illustrated in FIGS. 6 to 10, the cannula housing comprises two guide openings 14 and 15 and two locking openings 17 and 18 in addition to the rectilinear through bore 10. These openings are symmetrically shaped about a plane including the central axis 14 of the through passageway 13 and extending perpendicular to the rear side 6. The guide openings 15 and 16 are elongated openings of a substantially square cross section, cf. FIGS. 6, 8, and 10, which are adapted to receive mating guide pins 21 and 22 on the connecting hub 3, cf. FIG. 13. As illustrated in FIG. 8, the guide openings 15 and 16 are arranged inside the central projection 9 on the cannula housing 1 in such a manner that the orifices thereof in the illustrated embodiment are positioned on substantially the same plane as the inlet to the through passageway 13 with the central axis 14. The inlet of the through passageway 13 is indicated by the reference numeral 23.

Figure 11:
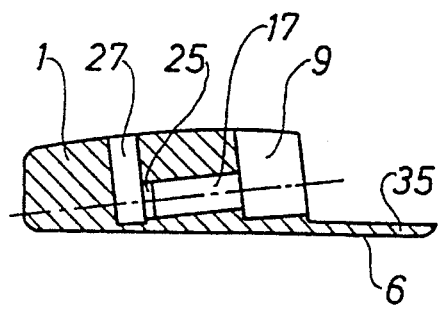
FIG. 11 is a sectional view taken along the line XI—XI of FIG. 8.

The locking openings 17 and 18 are of a relatively rectangular cross section gradually decreasing to a minimum value from the inlet on each side of the projection 9, the locking openings 17 and 18 adjacent the guide openings 15 and 16 and the central through bore 10 following a rectilinear course parallel to the central axis 14 and consequently also parallel to the guide openings 15 and 16. Immediately inside the minimum sectional area of the locking openings 17 and 18, said sectional area increases abruptly with the result that a shoulder 25 and 26, respectively, is formed. Immediately inside this shoulder, the sectional area decreases continuously while forming a curved bottom surface. The side surfaces of the locking openings 17 and 18 extending perpendicular to the symmetric plane through the central axis 14 are everywhere spaced the same distance from one another, whereby, however, the locking openings 17 and 18 at the bottom immediately inside the shoulders 25 and 26, cf. especially FIG. 11, are connected to the surface of the cannula housing through a shaft or channel 27 and 28, respectively, extending perpendicular from said locking openings 17 and 18.

Figure 13:
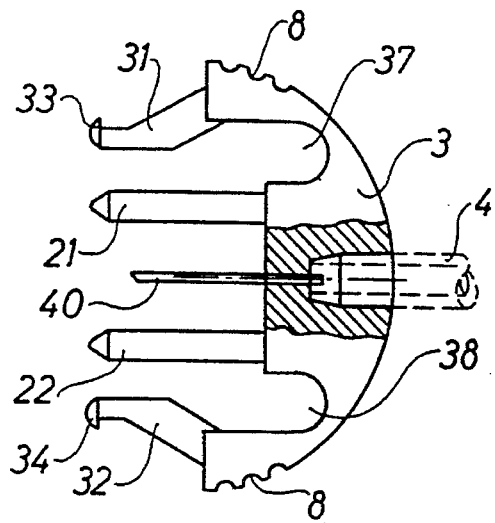

The locking openings 17 and 18 are adapted to receive mating symmetrically shaped locking pins 31 and 32 on the connecting hub 3. As illustrated in FIG. 13, these locking pins 31 and 32 comprise their respective barb-forming extension 33 and 34 for a locking engagement behind the shoulders 25 and 26, respectively, in the locking openings 17 and 18.

As illustrated in particular in FIGS. 6 to 11, the cannula housing 1 comprises a thin platform extending outwards in front of the portion in which the through bore 10 and the guide openings 16 and 16 and the locking openings 17 and 18 are shaped. This platform is designated the reference numeral 35 and is relatively thin and provided with a bottom side continuing into the bottom side of the remaining portion of the cannula housing 1 and thereby forming part of the rear side 6 of the infusion set. When seen from the top, the cannula housing 1 with the platform 35 is of a circular shape.

Figure 12:
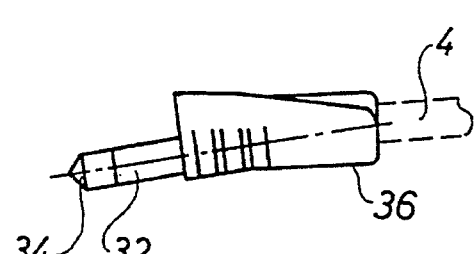
FIG. 12 is a side view of a connecting needle hub to be coupled to the cannula housing, FIG. 13 corresponds to FIG. 12, but whereby parts have been cut out for the sake of clarity.

As illustrated in FIGS. 7, 9, 10 and 11, both the through bore 10, the guide openings 15 and 16, and the locking openings 17 and 18 incline relative to the rear side 6, all the inlets thereof being placed farthest away from said rear side 6. This inclination is in the illustrated embodiment of the magnitude approximately 7°. Immediately outside the locking openings 17 and 18, the platform 6 is of a corresponding inclination, whereas it is shaped with a substantially plane top side extending parallel to the rear side 6 outside the projection 9. As illustrated in FIGS. 12 and 13, the guide pins 21, 22 and the locking pins 31 and 32 on the connecting hub 3 are of a corresponding inclination relative to the actual body of the connecting hub 3. The body of the connecting hub comprises a plane bottom side 36, which in the mounted state extends substantially parallel to the top side of the platform 35 on the cannula housing 1. As a result, the cannula housing 1 can be secured by means of a plaster placed across the platform 35.

As illustrated especially in FIG. 3, the locking pins 31 and 32 on the connecting hub 3 are shaped with a relatively small sectional area relative to the sectional area of the locking openings 17 and 18, whereby a relatively broad open channel is provided along the locking pins 31 and 32 when said locking pins engage the locking openings 17 and 18 in the cannula housing 1. This channel communicates freely with the shafts 27 and 28 in the cannula housing 1. FIG. 3 illustrates for the sake of clarity that the locking pins 31 and 32 with barbs 33 and 34 engage the shoulders 25 and 26 in the locking openings. The embodiment shown in FIGS. 6 to 10 of the cannula housing 1 does not render it possible to see the shoulders 25 and 26 through the shafts 27 and 28.

As illustrated in FIGS. 4 and 13, curve-shaped recesses 37 and 38 are shaped on each side of the locking pins 21 and 22. These recesses ensure that the locking pins 31 and 32 can be easily moved by means of finger forces into engagement with the shoulders 25 and 26 in the locking openings 17 and 18 and out of said engagement again by means of the finger forces of the patient.

FIG. 13 shows furthermore, that centrally the connecting hub 3 comprises a needle 40. When inserted through the membrane 12 in the cannula housing 1, this needle provides a connection between the hose 4 of the infusion set and the through passageway 13 of the cannula housing 1. As illustrated in FIG. 13, the length of the guiding pins 21 and 22 is longer than the freely projecting portion of the needle 40 with the result that during the coupling to the cannula housing 1 the connecting hub 3 is placed with the needle 40 in a centred position relative to the membrane 12 before said needle 40 is inserted through said membrane. In this manner it is ensured that the needle 40 is not damaged during the coupling procedure.

Figure 14:
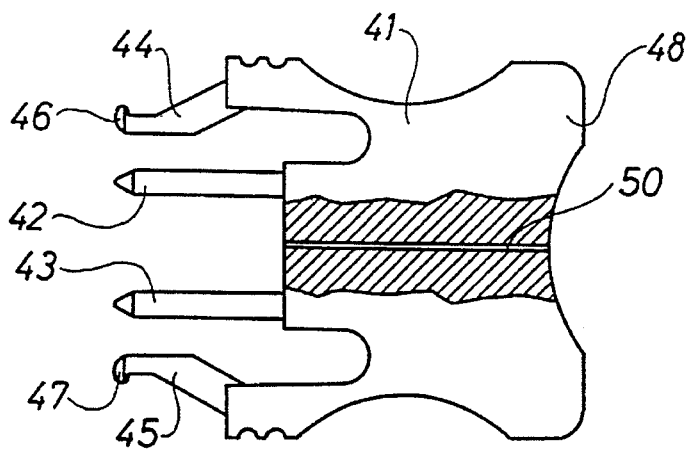
FIG. 14 is a top view of a preferred embodiment of an inserter hub to be coupled to the cannula housing so as to place said cannula housing on a patient, whereby parts have been cut out for the sake of clarity, and without an insertion needle.

An inserter needle hub is used for the insertion of the cannula 2 on the cannula housing 1 into the patient. Such an inserter needle hub appears from FIGS. 14, 15 and 16 at the reference numeral 41. This inserter needle hub is structured with completely the same shape as the connecting hub 3 with guide pins 42 and 43 and locking pins 33 and 45 with barbs 46 and 47. The portion of the inserter needle hub 41 adjacent the guide pins 42 and 43 and the locking pins 44 and 45 is also identical with the connecting hub 3 with the result that the inserter needle hub 41 completely fits in the cannula housing 1 and the locking pins 44 and 45 possess the necessary flexibility. The inserter needle hub 41 is only distinguished from the connecting hub 3 by comprising an extension 48 opposite the guide pins 42, 43 and the locking pins 44 and 45, said extension being of a suitable shape ensuring an easy retaining by means of the fingers and allowing an easy handling of the inserter needle hub 41.

Figure 15:
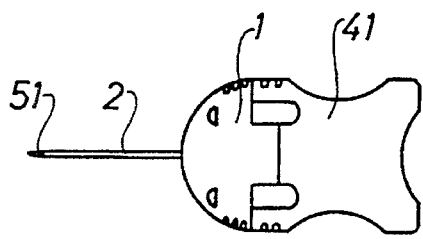
FIG. 15 is a top view of the inserter hub of FIG. 14 together with an insertion needle engaging a cannula housing.
Figure 16:
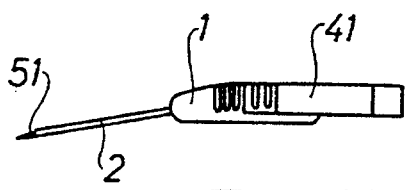
FIG. 16 is a side view of the inserter hub of FIG. 15.

Centrally, the inserter needle hub 41 comprises a through opening receiving an insertion needle. This insertion needle is not shown in FIG. 14 for the sake of clarity, but as shown in FIGS. 15 and 16 showing the inserter needle hub 41 coupled to the cannula housing 1 with the cannula 2, the insertion needle is of such a length, cf. the reference numeral 51, that the point projects outside the cannula 2. As a result, the cannula 2 can be inserted through the skin of a patient in a conventional manner. When the cannula 2 is correctly positioned in the patient, it is left there together with the associated cannula housing 1, whereas the inserter needle hub is removed. Subsequently, the cannula housing 1 is used together with the connecting hub 3 being coupled thereto when it is desired to administer a suitable therapeutical substance, such as insulin from a pump.

The cannula housing 1 can also be used for administration of medicines by means of a syringe, the needle of which is inserted through the membrane, the inclination of the through passageway 13 in the cannula housing 1 allowing an easy performance thereof. The connecting hub 3 is easily moved into engagement with the cannula housing 1 by the guide pins 21 and 22 and the locking pins 31 and 32 being inserted in the associated guide openings 15 and 16 and locking openings 17 and 18. During this procedure, the barbs 33 and 34 of the locking pins 31 and 32 slide against the outer oblique surfaces in the locking openings 17 and 18 and are pressed against one another until they grip behind the shoulders 25 and 26 by a snap-effect. During this coupling movement, the needle 40 passes automatically through the membrane 12, cf. FIG. 5, with a correct central positioning, whereby the point of the needle does not hit the sides of the bushing 11.

When the connecting hub 3 is to be removed from the cannula housing 1, the user presses the locking pins 31 and 32 relatively easily together in such a manner that the barbs 33 and 34 can pass the shoulders 25 and 26 in the locking openings 17 and 18.

The cannula housing 1 is left secured to the skin of the patient by means of suitably shaped plasters extending across the platform 35 and across the body of the cannula housing 1. Such a plaster material is suitably shaped with openings or recesses for uncovering the shafts 27 and 28 to the locking openings 17 and 18 in such a manner that dirt is not collected therein and water can easily pass out during bathing.

According to a preferred embodiment of the invention, the cannula housing 1 and the connecting hub 3 of the infusion set are in the assembled state of an outer diameter of 21 mm and a height of 5 mm. The volume behind the membrane in the through passageway 13 fills approximately 0.003 ml, whereby the waste of the therapeutical substance is reduced to a minimum during the administration. The cannula housing 1 and the connecting hub 3 are made of a suitable plastic material, such as polypropylene.

The cannula housing 1 with the platform 35 provides a large and homogenous contact surface, whereby the pressure effect against the skin is minimized. As a result, the user convenience is increased and the risk of possible pressure wounds has been minimized.

The individual members can be assembled without the use of glue, whereby the risk of possible allergic reactions caused thereby is minimized. The position of the membrane 12 in immediate vicinity of the inlet 23 to the through passageway 13 at the outer side of the projection 9 reduces the risk of dirt and other foreign bodies from penetrating therein.

The invention has been described with reference to a preferred embodiment. Many modifications can be carried out without thereby deviating from the scope of the invention.

I claim:

1. An infusion set for an intermittent or continuous administration of a therapeutical substance, such as insulin, said infusion set comprising a cannula housing with a soft plastic cannula to be placed inside the body of a patient, where the cannula together with the cannula housing form a through passageway the inlet of which into the cannula housing is covered by a membrane, and where said infusion set comprises a needle hub with a needle to be inserted in the through passageway of the cannula housing through the membrane, and furthermore guide means for centering the needle relative to the membrane and the through passageway, as well as locking means for releasably interlocking the cannula housing and the needle hub, characterised in that in the assembled state the cannula housing (1) and the needle hub (3, 41) present a substantially planar rear side (6) and a relatively large width in a direction parallel thereto and substantially perpendicular to the longitudinal central axis (14) of the through passageway (13), that the guide means (15, 116, 21, 22, 42, 43) are co-operating guide pins (21, 22, 42, 43) and guide openings (15, 16) on each side of the needle (40, 51) and the through passageway (13), and that the locking means (31, 32, 44, 45) are resilient locking pins (31, 32, 44, 45) arranged on their respective side of the needle (40, 51) on the needle hub (3, 41) and comprising barbs (33, 34, 46, 47), said locking pins with barbs being adapted to be received in their respective recess (17, 18) in the cannula housing (1), where said recesses comprise shoulders (25, 26) mating said barbs (33, 34, 46, 47).

2. An infusion set as claimed in claim 1, characterised in that the cannula housing (1) and the needle hub (3, 41) in the assembled state are of a substantially circular shape with a substantially uniform thickness, the cannula housing being formed integral with a projecting platform (35) substantially covering the entire rear side (6) of the needle hub (3, 41) in the assembled state.

3. An infusion set as claimed in claim 2, characterised in that the cannula housing (1) and the needle hub (3, 41) in the assembled state are divided along a substantially diametrically extending plane, which extends perpendicular to the central axis (14) of the needle (40, 51) and the through passageway (13), whereby the inlet (23) to the through passageway (13) and to the guide openings provided in the cannula housing is shaped in a projection (9) extending perpendicular from the diametrical plane and into a corresponding recess in the needle hub (3, 41).

4. An infusion set as claimed in claim 1, characterised in that the guide pins (21, 22; 42, 43) with the associated guide openings (15, 16) and the locking pins (31, 32; 44, 45) with corresponding recesses (17, 18) are symmetrically shaped relative to a central plane perpendicular to the plane rear side (6) and coinciding with the longitudinal central axis of the needle (40; 51) and the through passageway (13).

5. An infusion set as claimed in claim 1, characterised in that the locking pins (31, 32; 44, 45) and the guide pins (21, 22; 42, 43) are placed on the needle hub (3; 41) and the barbs (33, 34, 46, 47) of the locking pins (31, 32, 44, 45) face away from one another, and that symmetrically shaped recesses (37, 38) are provided between the locking pins (31, 32; 44, 45) for increasing the flexibility of the locking pins (31, 32; 44, 45).

6. An infusion set as claimed in claim 1, characterised in that the recesses (17, 18) for receiving the locking pins (31, 32) everywhere have a larger sectional area than the locking pins (31, 32) and at the bottom immediately adjacent the shoulders (25, 26) co-operating with the barbs (33, 34; 46, 47) on the locking pins (31, 32; 44, 45) communicate with the top side of the portion in question of the infusion set through an opening (27, 28).

7. An infusion set as claimed in claim 1, characterised in that the longitudinal central axis (14) of the through passageway (13) inclines relative to the plane rear side (6), the inlet end (23) with the membrane (12) being positioned farthest away from said plane rear side (6) relative to the location where the cannula (2) exits the cannula housing (1), and that the guide means (15, 16, 21, 22; 42, 43), the locking means (17, 18, 31, 32; 42, 43), and the needle (40, 51) on the needle hub (3, 41) may incline correspondingly at the same time.

8. An infusion set as claimed in claim 1, characterised in that the needle hub (41) with a needle (51) is shaped in form of an inserter needle hub to be used when the cannula (2) of the cannula housing (1) is to be placed in the body of the patient, the needle (51) of the inserter needle hub (41) extending all through the through passageway (13) and projecting outside the free end of the cannula (2), and that at the same time the inserter needle hub (41) may comprise an extension (48) projecting away from the locking means and facilitating the handling of the infusion set during the placing.

* * * * *

UNITED STATES PATENT AND TRADEMARK OFFICE
CERTIFICATE OF CORRECTION

PATENT NO. : 5,522,803
DATED : June 4, 1996
INVENTOR(S) : Claude Teissen-Simony

It is certified that error appears in the above-indentified patent and that said Letters Patent is hereby corrected as shown below:

On the Title Page item [73], Assignee, please delete "Pharma Plast" and substitute --Pharma-Plast--.

Signed and Sealed this

Fourth Day of February, 1997

Attest:

BRUCE LEHMAN

Attesting Officer     Commissioner of Patents and Trademarks